United States Patent [19]

Chartrain et al.

[11] Patent Number: 5,474,919
[45] Date of Patent: Dec. 12, 1995

[54] **BIOCONVERSION PROCESS FOR THE SYNTHESIS OF TRANSHYDROXY SULFONE BY *RHODOTORULA RUBRA* OR *RHODOTORULA PILIMINAE***

[75] Inventors: Michel M. Chartrain, Westfield; Lorraine G. Katz, Springfield; Steven A. King, Summit, all of N.J.

[73] Assignee: Merck & Co., Inc., Rahway, N.J.

[21] Appl. No.: 305,110

[22] Filed: Sep. 13, 1994

[51] Int. Cl.⁶ .............................. C12P 17/16; C12N 1/16; C12N 1/00
[52] U.S. Cl. .................. 435/118; 435/911; 435/255.1
[58] Field of Search ................... 435/118, 911, 435/255.1

[56] References Cited

U.S. PATENT DOCUMENTS

| | | | |
|---|---|---|---|
| 4,797,413 | 1/1989 | Baldwin et al. | 514/432 |
| 4,968,814 | 11/1990 | Blacklock et al. | 549/66 |
| 4,968,815 | 11/1990 | Blacklock et al. | 549/66 |
| 5,091,409 | 2/1992 | Baldwin et al. | 514/434 |
| 5,157,129 | 10/1992 | Blacklock et al. | 549/23 |
| 5,352,579 | 10/1994 | Milliman | 435/6 |
| 5,356,812 | 10/1994 | Matsayama et al. | 435/280 |
| 5,371,014 | 12/1994 | Matsayama et al. | 435/280 |

FOREIGN PATENT DOCUMENTS

| | | |
|---|---|---|
| 590549 | 4/1994 | European Pat. Off. . |
| WO94/05802 | 3/1994 | WIPO . |

*Primary Examiner*—Marian C. Knode
*Assistant Examiner*—Mike Meller
*Attorney, Agent, or Firm*—Sylvia A. Ayler; Mark R. Daniel

[57] ABSTRACT

There is disclosed a novel microbial bioconversion process for the synthesis of a trans-hydroxy sulfone intermediate, which is the precursor to topical carbonic anhydrase inhibitors (TCAI's). TCAI's are effective in the treatment of glaucoma and ocular hypertension. The bioconversion process is carried out in the presence of the microorganism *Rhodotorula rubra*, or *Rhodotorula piliminae* and results in a trans-hydroxy sulfone which exhibits a diastereomeric excess of greater than 95%.

7 Claims, No Drawings

BIOCONVERSION PROCESS FOR THE SYNTHESIS OF TRANSHYDROXY SULFONE BY *RHODOTORULA RUBRA* OR *RHODOTORULA PILIMINAE*

BACKGROUND OF THE INVENTION

Glaucoma is in ocular disorder associated with elevated intraocular pressures which are too high for normal fimction and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Compounds of structural Formula:

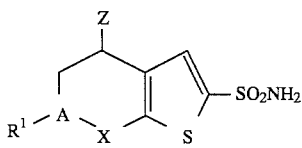

the individual diastereomers, the individual enantiomers or mixtures thereof, or an ophthalmologically acceptable salt thereof, wherein:

A is carbon or nitrogen;

Z is NHR or —OR;

R is $C_{1-6}$ alkyl, either straight or branched chain;

$R^1$ is
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl; and X is —SO2— or —C(O)—;

are known from U.S. Pat. Nos. 4,797,413 and 5,157,129. The compounds are known to be topically effective carbonic anhydrase inhibitors (TCAI's) useful in the treatment of ocular hypertension. The synthesis of the compounds involves the reduction of a sulfo-ketone to a trans-hydroxy sulfone precursor to the above-noted compounds. However, the synthetic processes described for their preparation result in diastereomeric or racemic products which must be separated and resolved, with concomitant loss of at least 50% of the product, to obtain the most active enantiomer.

Now with the present invention there is provided a novel microbial process for the bioconversion of the sulfo-ketone intermediate to a trans-hydroxy sulfone intermediate.

SUMMARY OF THE INVENTION

This invention is concerned with a novel microbial bioconversion process for synthesis of trans-hydroxy sulfone having the structural formula:

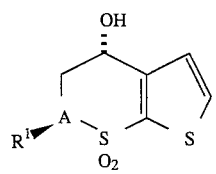

wherein A and $R^1$ are as described above. The trans-hydroxy sulfone is the precursor to the final product, a carbonic anhydrase inhibitor of Formula I above. The final product is topically effective in the treatment of ocular hypertension and glaucoma. The process comprises fermentation of the sulfo-ketone substrate in the presence of the microorganism *Rhodotorula rubra*, (ATCC 74283); or *Rhodotorula pilirninae* (ATCC 32762), preferably *Rhodotorula rubra*. The biotransformation is accomplished under submerged aerobic conditions in an aqueous carbohydrate medium containing a nitrogen nutrient at a pH of about 4.5 to 8.0, preferably 6.0, for a sufficient time to produce the compound of structural formula II.

The resultant trans-hydroxy sulfone analog exhibits a diastereomeric excess of greater than 95%. The key step in this novel process, (i.e., control of the diastereomeric excess of the hydroxy sulfone), is controlling the residual sulfoketone concentration in the bioconversion reaction medium.

Thus it is an object of the present invention to provide a microbial process for the synthesis of the trans-hydroxy sulfone intermediate.

DETAILED DESCRIPTION OF THE INVENTION

This invention is concerned with the synthesis of the compounds of structural formula:

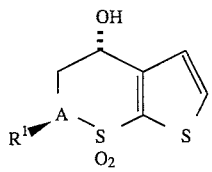

wherein A is carbon or nitrogen and $R^1$ is:
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl, which is the precursor to compounds represented by Formula:

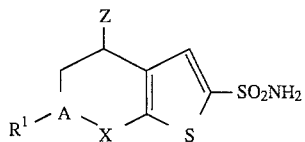

the individual diastereomers, the individual enantiomers or mixtures thereof, or an ophthalmologically acceptable salt thereof, wherein:

A is carbon or nitrogen;

Z is NHR or —OR;

R is $C_{1-6}$ alkyl, either straight or branched chain;

$R^1$ is
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl; and X is —$SO_2$— or —C(O)—;

The novel process of this invention comprises fermentation of the microorganism *Rhodotorula piliminae* or *Rhodotorula rubra*, preferably *Rhodotorula rubra* in the presence of substrate Compound III as shown:

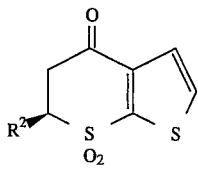

Sulfo-Ketone-III wherein R² is
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl in a nutrient medium, under aerobic conditions until a substantial amount of Compound II is produced and isolating the compound so produced in a conventional manner. The compounds of structural formula I are used to treat glaucoma.

A preferred embodiment of this invention, where a compound represented by Formula II:

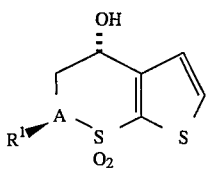

wherein A is carbon or nitrogen and R¹ is:
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl,
which is the precursor to compounds represented by Formula I:

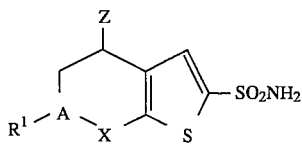

the individual diastereomers, the individual enantiomers or mixtures thereof, or an ophthalmologically acceptable salt thereof, wherein:

A is carbon or nitrogen;
Z is NHR or —OR;
R is $C_{1-6}$ alkyl, either straight or branched chain;
R¹ is
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl; and X is —$SO_2$— or —C(O)—;

comprises the steps of culturing a microorganism *Rhodotorula rubra*, ATCC 74283 in a nutrient medium containing assimilable sources of nitrogen and carbon and substrate Compound III:

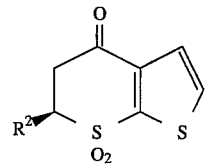

wherein R² is
  a) $C_{1-5}$ alkyl, either straight or branched chain, especially n-propyl or isobutyl;
  b) $C_{3-5}$ alkenyl, especially allyl;
  c) $C_{3-5}$ alkynyl, especially propargyl;
  d) hydrogen; or
  e) $C_{1-4}$ alkoxy-$C_{1-4}$ alkyl
under aerobic conditions until a substantial amount of Compound II is produced and isolating the compound so produced, wherein the substrate is dissolved in from about 1% to about 15% v/v of ethanol, methanol or DMSO, and the amount of substrate charged is from about 1 to about 3 g/L, the temperature is from about 20° to about 50° C., and the pH is from about 4.5 to 8.0.

The substrate Compound III can be synthesized in the following non-limiting manner:

Methyl 3(R)-hydroxyhexanoate

Methyl 3-ketohexanoate (44.7 g, 310 mmol) was diluted with methanol (75 mL) and 0.2N HCl (2 mL). $Et_2NH_2^+$ $Ru_2Cl_{5-}$ $(BINAP)_2$ (200 mg) was added and the mixture was heated at 60° under 100 psi of hydrogen for 2 hours. Toluene (100 mL) was added and the mixture was concentrated to an oil weighing 75 g.

Methyl 3(R)-toluenesulfonyloxyhexanoate

The crude solution of methyl 3(R)-hydroxyhexanoate (310 mmol) was dissolved in pyridine (100 mL) and p-toluenesutfonyl chloride (59 g, 310 mmol) was added. The mixture was stirred at 5° for 24 h and then 15° for 16 h. Water (5 mL) was added slowly over 1 h to quench excess reagent. The mixture was poured into 20% toluene/hexane (600 mL) and washed with water (3×250 mL). The organic layer was concentrated to yield 83 g of the product as an oil which was 95% pure.

Methyl 3(S)-(2-thiophenethio)hexamoate n-Butyl lithium (1.64M, 97.6 mL, 160 mmol) was added to thiophene (15.1 g, 180 mmol) in THF (100 mL) at −20°. After stirring for 30 minutes, sulfur (5.23 g) was added portionwise. After 1 h deoxygenated formamide (100 mL) was added followed by methyl 3(R)-toluenesulfonyloxyhexanoate (40 g, 33.3 mmol). The mixture was stirred at room temperature for 24 h and then diluted with ethyl acetate (100 mL) and water (50 mL). The layers were separated and the aqueous was backextracted with ethyl acetate (100 mL). The combined organics were concentrated to give the product as a yellow oil weighing 23.9 g. The overall yield from methyl 3-ketohexanoate was 74%.

5,6-Dihydro-6(S)-(propyl)-4 H-thieno[2,3b]thiopyran-4-one

Methyl 3(S)-(2-thiophenethio)hexanoate (125 g, 513 mmol) was heated at 100° C. with acetic acid (150 ml) and concentrated HCl (150 mL) for 96 h. The mixture was extracted with toluene (2×300 mL). The combined organic layers were washed and concentrated to give a dark brown oil which was taken up in toluene (1200 mL). The mixture was cooled to 0° and trifluoroacetic anhydride (126 g, 600 mmol) was added. After 45 minutes the mixture was washed with water (2×200 mL) and concentrated to give 151 g of oil which was carded to the next step without purification.

5,6-Dihydro-6(S)-(propyl)-4H-thieno[2,3b]thiopyran-4-one-7,7-dioxide 5,6-Dihydro-6(S)-(3-propyl)-4H-thieno[2,3b]thiopyran-4-one (4.25 g, 20 mmol) was dissolved in ethyl acetate (80 mL). Sodium tungstate (660 mg, 2 mmol), 30% hydrogen peroxide (8.2 mL, 80 mmol), and 10 drops of sulfuric acid were added. After 24 h the reaction was diluted with ethyl acetate (100 mL) and washed with 10% $Na_2SO_3$ solution and sat'd $NaHCO_3$ solution. The organic layer was concentrated and triturated with ethanol to give the product 4.5 g (95%).

Microorganisms

A biologically pure sample of *Rhodotorula piliminae* is isolated from the larva of *Drosophila pilimanae*, Hawaii and is currently available under the Budapest Treaty in the permanent culture collection of the American Type Culture Collection, 12301 Parklawn Drive in Rockville, Md., from which it is available under the Accession Number ATCC 32762. A biologically pure sample of *Rhodotorula rubra* is currently available in the permanent culture collection of the American Type Culture Collection, 12301 Parklawn Drive in Rockville, Md., from which it is available under the Accession Number ATCC 74283. Any restrictions relating to public access to the microorganism shall be irrevocably removed upon a patent grant. *Rhodotorula rubra* ATCC 74283 was isolated from contaminated sour cream.

The analytical methods generally employed in the present invention, though non-limiting, were as follows:

Analytical Methods Biomass Measurements

Biomass was measured by optical density and cell dry weight. Optical density measurements were performed using a Hewlett Packard 8451A diode array spectrophotometer set at 660 nm. Cell dry weights were measured using Millipore filters type HA, pore size 0.45 μm.

Glucose

Glucose was monitored by a liquid chromatograph equipped with a Macintosh classic computer for control and data acquisition, a refractive index detector, an Al-2 Dynamax autoinjector, an analytical HP pump, a pressure module and a Biorad Aminex HPX- 87H ion exclusion (300×78 mm) column heated at 60° C. The eluant consisted of 0.005M sulfuric acid at 0.7 mL/minutes.

Broth Extraction

Whole broth was extracted by adding an equal volume of ethyl acetate. The mixture was placed on a shaker for 5 minutes then centrifuged at 2000 rpm for 10 minutes using a Beckman TJ-6 centrifuge. The resulting supernatant was dried and resuspended in methanol for thin layer chromatography or HPLC analysis.

Thin Layer Chromatography

Kiesel precoated silica gel 60 thin layer chromatography plates F254 were used. The mobile phase consisted of 94% methylene chloride, 5% methanol and 1% ammonium hydroxide. Samples were spotted on the plate and dried. One edge of the plate was immersed in the mobile phase, and the solvent was allowed to run up the plate until about an inch before the top of the plate.

High Performance Liquid Chromatography

HPLC was performed with a Rainin system equipped with a Macintosh classic computer for control and data acquisition, Dynamax absorbance detector UV-M, an Al-2 Dynamax autoinjector, two analytical HP pumps, a pressure module equipped with a Zorbax RX-C8 column (4.6×250 nm), that was maintained at room temperature. The method employed two eluants, methanol and water (0.1% v/v $H_3PO_4$) at a combined flow rate of 1.5 mL/minutes and UV detection at 254 nm. The method consisted of a gradient 30/70 of methanol/acidified water (v/v) to 70/30 (v/v) over 15 minutes. It was maintained at 70/30 (v/v) for 5 minutes then equilibrated to 30/70 (v/v) for 5 minutes. The method separates cis-hydroxy sulfone, trans-hydroxy sulfone and sulfo-ketone at 9.5, 10 and 12.8 minutes, respectively.

EXAMPLE 1

Cultivation Methods

The production of the trans-hydroxy sulfone occurred for example during screen or shake flask cultivation, *Rhodotorula rubra* ATCC 74283 cells were inoculated originally from Sabouraud dextrose (Difco) slants or later from frozen glycerol cell suspensions (1 mL) into 250 ml Eriemeyer flasks containing 50 mL of Sabouraud dextrose broth. The Sabouraud dextrose broth is commercially available and is composed of 10 g/L Difco neopeptone and 20 g/L Bacto dextrose. The flasks were incubated for 24 hours at 28° C., with a 220 rpm agitation in order to obtain sufficient biomass for use as an inoculum. The inoculum was transferred (5%/25 mL) into a 2 liter Eriemeyer flask containing 500 mL of Sabouraud dextrose broth. Then, the culture was incubated at 28° C. with 180 rpm agitation for 42 hours. The cells were centrifuged, washed with MES buffer pH 6.0 and resuspended in MES buffer pH 6.0 before the addition of the sulfo-ketone.

Bioreactor Cultivation was carried out in a 23 liter fermentor which was inoculated with a 2 liter flask of Sabouraud dextrose broth containing *Rhodotorula rubra* ATCC 74283 cultivated for 42 hours as previously described. The fermentor parameters were as follows: temperature 28° C., agitation 200 rpm (minimum set point), aeration 10 L/minutes and back pressure 0.6 psi. The dissolved oxygen tension was controlled by agitation at a minimum of 40%. When the oxygen uptake rate (OUR) dropped below 5 mmoles/L/hr, the cells were harvested using sterile conditions.

Reaction parameters

Optimum bioconversion parameters are those in which 3-[N-Morpholino] propanesulfonic acid (MOPS) or 2-[N-Morpholino] ethanesulfonic acid (MES) buffers (0.5M) are used at about 20° to about 40° C. in a pH range of 4.5 to 8.0, resulting in bioconversion rates of about 0.011 g/g CDW/hr to about 0.150 g/g CDW/hr. The temperature range is from about 20° to about 50° C., preferably from about 30° to about 35° C. The solvent employed and the amount used to dissolve the sulfo-ketone substrate are ethanol, methanol or DMSO, preferably DMSO between 1% to 15% v/v, preferably 1% to 3%, respectively. The amount of substrate charged is from about 1 to about 3 g/L, preferably 1.5 g/L to achieve recovery of trans-hydroxy sulfone (66%) having a diastereomeric excess of 95%; and the cells are aged about 16 to 60 hours, preferably around 40 to 60 hours, corresponding to the OUR dropping below 5 mmoles/L/hr.

Bioconversion and Isolation of Trans-Hydroxy Sulfone II (5,6 di-hydro-4(S)-hydroxy-6(S)-propyl-4H-thieno-[2,3-b]thio-pyran,7,7 dioxide)

Aliquots of the broth (10 or 50 mL) containing *Rhototorulo rubra* cells were centrifuged at 4000 rpm for 10 minutes using a Beckman TJ-6 centfifuge and the supematant decanted. The pellet was resuspended in 0.5M 2-[N-morpholino] ethanesulfonic acid (MES) buffer at a pH of 6.0 and centrifuged again. The washed cells were resuspended in 50 mL MES buffer. When needed, the cells were diluted to achieve better analysis of the bioconversion reaction rates. Crude sulfo-ketone substrate (56% purity) equivalent to 1 g/L of pure sulfo-ketone dissolved in ethanol (3% v/v ) was added to the flasks containing washed cells. The flasks were incubated in a water bath of 32.5° C. that was continuously shaken. The broth was harvested by extraction with chloroform ( 1:1, v/v) or ethyl acetate ( 1:1, v/v) dried and resuspended in methanol. Thin layer and high performance liquid chromatography (HPLC) analyses were then conducted on the extracts. The HPLC retention times for the trans-hydroxy sulfone, the cis-hydroxy sulfone and the sulfoketone were 9.5, 10.0 and 12.8, respectively. $^1$H NMR results for the trans-hydroxy sulfone (250 MHz, CDCl$_3$) are shown below:

δ7.58 (d, J=5.1 Hz, 1H), 7.08 (d, J=5.1 Hz, 1H), 4.94 (t, J=3.6 Hz, 1H), 3.66 (m, 1H), 2.6–2.1 (m, 3H), 1.7–1.5 (m 3H), 1.01 (t, J=7.01, 3H).

With Bioreactor cultivation the cells were harvested when the OUR dropped below 5 mmoles/L/hr, centrifuged and washed with 0.5M MES buffer pH 6.0. The cells were resuspended in 0.5M MES buffer pH 6 and returned to the fermentor. The fermentor parameters were set for bioconversion as follows: temperature of 32.5° C., agitation 400 rpm and aeration 6 L/minutes and back pressure 0.6 psi. Sulfo-ketone (1.5 g/L) was dissolved in DMSO and added to the fermentor (3% v/v). Samples were taken periodically to monitor bioconversion activity by HPLC. A bioconversion rate of 1.14 g/L/hr or 0.126 g/g CDW/hr and a final yield of trans-hydroxy sulfone of 1.04 g/L-1 having a 96.4% diastereomeric excess was achieved at harvest. The broth was extracted with ethyl acetate (0.5:1, v/v) and the solvent phase was concentrated using a rotavap.

EXAMPLE 2

Bioconversion of trans-hydroxysulfone (5,6 dihydro-4(S)-hydroxy- 6(S)-methy-4H-thieno-[2,3-b] thio-pyran, 7,7 dioxide)

Cells of culture ATCC 74283 preserved on slants of Sabouraud dextrose agar at 4° C. were used to inoculate a 250 ml Erlenmeyer flask containing 50 ml of Sabouraud dextrose broth. After an incubation of 20 hours at 28° C. while shaking, the ketosulfone dissolved in ethanol (33.3 mg/ml) was added to the flasks (1 ml per flask). The cultures were returned to the same incubation conditions for an additional 24 hours. Residual ketosulfone and produced hydroxysulfone were extracted from the broth with one volume of chloroform. TLC and HPLC analyses indicated the total conversions of the sulfoketone to the trans-hydroxysulfone. NMR analyses confirmed the structure of the trans-hydroxysulfone:

δ7.6 (d, 1H, C$_2$-H), 7.1 (d, 1-H, C$_3$-H), 4.9 (m, 1H, C$_4$-H), 3.8 (m, 1H, C$_6$-H), 3.5–3.0 (br s, 1H, OH), 2.6 (m, 1H, C$_5$-H), 2.4 (m, 1H, C$_5$-H), 1.5 (d, 3H, C$_6$-CH$_3$).

EXAMPLE 3

By way of example, the process for making the compounds of formula I [5,6 dihydro-6-(S)-propyl-4(S)-1-ethylamino-4H-thieno-[2,3-b]thio-pyran-2-sulfonamide 7,7-dioxide] is as follows:

Step 1: Procedure:
Trans-hydroxysulfone (7.32 g, 29.7 mmol) is suspended in acetonitrile (38 mL) in a 100 mL round bottom flask equipped with a magnetic stirrer, a thermocouple probe and a nitrogen inlet. The solution is cooled to 0° C. and sulfuric acid (5 ml, 88.7 mmol) is added in portions. The reaction mixture is then stirred at room temperature. The mixture is cooled to 0°–5° C. A 500 mL flask is charged with water (34 mL) and acetonitrile (43 mL) next the mixture is cooled to 0°–5° C. and stirred well. The reaction mixture is then added carefully so the quench temperature remains below 5° C. Saturated potassium carbonate (30 mL) is then added until the pH of the aquous layer is between 7–8 or until there is no more carbon dioxide evolution. The organic layer is concentrated to a crude oily material (14.1 g) which assays at 42.5 weight %. The yield is 5.99 g (73%).

Step 2: Procedure:
A 100 mL round flask, equipped with a magnetic stirrer and a thermocouple probe, is charged with chlorosulfonic acid (13.14 mL) and the acid is cooled to 0°–5° C. The acetamidosulfone (6.57 g) is added portionwise over 30 minutes so the internal temperature is below 15° C. The dark reaction mixture is then heated to 33° C. for 16 h, and then for 5 h to 50° C. When HPLC shows that <0.5% (versus sulfonic acid and sulfonyl chloride) of acetamidosulfone remains, the mixture is cooled to room temperature. Thionyl chloride (13.14 mL) is then added dropwise. After the addition is complete, the dark mixture is heated to 45° C. After 16 h, less than 0.5 area % of sulfonic acid remains. The mixture is cooled to 0°–5° C. A 1 L flask is charged with water (325 mL), and cooled to 0° C. The chlorination mixture is then added dropwise over 30 minutes to the well-stirred quenching solution so the internal temperature remains below 5° C. The mixture is stirred for 45 minutes and then filtered. The wet cake is wash with cold water (10 mL) and dried under flowing nitrogen. Concentrated aqueous ammonia (24 mL) and THF (43 mL) are charged to a 250 mL flask equipped with a magnetic stirrer and a thermocouple probe. The mixture is cooled to ca −10° C. The crude sulfonylchloride wet solid is added portionwise over 1 h with an internal temperature maintained below 0° C. After 2 h less than 1.8% of Sulfonylchloride remains. The excess of ammonia is neutralized with aqueous hydrochloric acid (ca 50 mL). The aqueous layer is washed with THF twice. The THF layers are combined and concentrated. The material is suspended again in THF and water is added carefully. Brown crystals form and a yellow aqueous solution remains. The mixture is filtered and the crystals are dried in vacuo. The yield of acetamidosulfonamide is 5.58 g (66%).

Step 3: Procedure:

Acetamidosulfonamide (4.21 g, 11.5 mmol) is dried by distillation with THF (2×100 mL portions) in a 250 mL flask. The flask is equipped with a magnetic stirrer, a thermocouple probe and a nitrogen inlet. The acetamidosulfonamide suspension in 22.5 mL of THF is then cooled to 0°–5° C. Borane-THF (51 mL, 51 mmol) is added dropwise over 45 minutes while maintaining the internal temperature below 5° C. After the evolution of hydrogen is complete (20 minutes), the solution is warmed to 30°–35° C. After the reaction is complete (3 h), the mixture is cooled to room temperature. A 250 mL, round bottom flask, equipped with magnetic stirrer, thermocouple probe and nitrogen inlet, is charged with sulfuric acid (60 mL) and cooled to 0°–5° C. The reduction mixture is then metered carefully into the well-stirred acid solution while the internal temperature is maintained below 20° C. After the addition, the mixture is stirred at room temperature until the evolution of hydrogen is complete. The flask is then set for distillation (1 atm) and the mixture concentrated until the internal temperature is >97° C. After the distillation is complete, the mixture is cooled to 20° C. The mixture is then neutralized with aqueous potassium bicarbonate and extracted with ethyl acetate (100 ml). The organic layer is concentrated to yield 3.45 g of 5,6 dihydro-6-(S)-propyl-4(S)-1-ethylamino-4H-thieno [2,3-b] thiopyran-2-sulfonamide 7,7-dioxide.

What is claimed is:

1. A process for the preparation of a compound of Formula II:

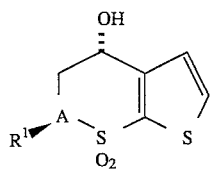

wherein A is carbon or nitrogen and $R^1$ is:
a) $C_{1-5}$ alkyl, either straight or branched chain;
b) $C_{3-5}$ alkenyl;
c) $C_{3-5}$ alkynyl;
d) hydrogen; or
e) $C_{1-4}$ alkoxy-$C_{1-4}$ alkyl,
comprising the steps of culturing a microorganism selected from the group consisting of *Rhodotorula rubra*, ATCC 74283 and *Rhodotorula piliminae* ATCC 32762 in a nutrient medium containing assimilable sources of nitrogen and carbon and a substrate of Formula III:

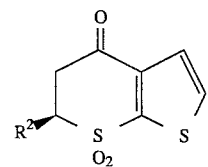

wherein $R^2$ is
a) $C_{1-5}$ alkyl, either straight or branched chain;
b) $C_{3-5}$ alkenyl;
c) $C_{3-5}$ alkynyl;
d) hydrogen; or
e) $C_{1-4}$ alkoxy-$C_{1-4}$ alkyl
under aerobic conditions until a recoverable amount of the compound of Formula II is produced and isolating the compound of Formula II.

2. The process of claim 1 wherein the microorganism is *Rhodotorula rubra*, ATCC 74283, the substrate is dissolved in from about 1% to about 15% v/v of ethanol, methanol or DMSO, and the amount of substrate is from about 1 to about 3 g/L.

3. The process of claim 2 wherein the substrate is dissolved in from about 1% to about 3% v/v of DMSO and the amount of substrate is from about 1 to about 3 g/L.

4. The process of claim 1 wherein the temperature is from about 20° to about 50° C., and the pH is from about 4.5 to 8.0.

5. The process of claim 1 wherein the temperature is from about 30° to about 35° C. and the pH is from about 5.5 to about 6.5.

6. A process for the preparation of a compound of Formula II:

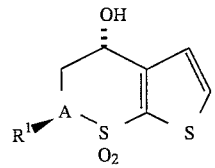

wherein A is carbon or nitrogen and $R^1$ is:
$C_{1-5}$ alkyl, either straight or branched chain;
b) $C_{3-5}$ alkenyl;
c) $C_{3-5}$ alkynyl;
d) hydrogen; or
e) $C_{1-4}$ alkoxy-$C_{1-4}$ alkyl,
comprising the steps of culturing *Rhodotorula rubra*, ATCC 74283 in a nutrient medium containing assimilable sources of nitrogen and carbon and a substrate of Formula III:

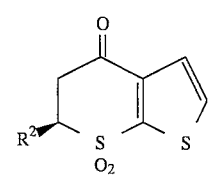

wherein $R^2$ is
a) $C_{1-5}$ alkyl, either straight or branched chain;
b) $C_{3-5}$ alkenyl;
c) $C_{3-5}$ alkynyl;
d) hydrogen; or
e) $C_{1-4}$ alkoxy-$C_{1-4}$ alkyl
under aerobic conditions until a recoverable amount of the compound of Formula II is produced and isolating the compound of Formula II, wherein the substrate is dissolved in from about 1% to about 15% v/v of ethanol, methanol or DMSO, and the amount of substrate is from about 1 to about 3 g/L, the temperature is from about 20° to about 50° C., and the pH is from about 4.5 to 8.0.

7. The process of claim 6 wherein the substrate is dissolved in from about 1% to about 3% v/v of DMSO, the amount of substrate is from about 1 to about 3 g/L, the temperature is from about 30° to about 35° C. and the pH is from about 5.5 to about 6.5.

* * * * *